(12) United States Patent
Nakaso et al.

(10) Patent No.: US 7,647,814 B2
(45) Date of Patent: Jan. 19, 2010

(54) ENVIRONMENT DIFFERENCE DETECTOR

(75) Inventors: Noritake Nakaso, Kitakatsushika-gun (JP); Shingo Akao, Kitakatsushika-gun (JP); Kazushi Yamanaka, 6-3, Katsura 2-chome, Izumi-ku, Sendai-shi, Miyagi 981-3134 (JP); Dong Youn Sim, Fujisawa (JP); Ichitaro Satoh, Tokyo (JP); Tetsuya Miyagishi, Tokyo (JP)

(73) Assignees: Toppan Printing Co., Ltd., Tokyo (JP); Kazushi Yamanaka, Sendai (JP); Yamatake Corporation, Tokyo (JP); Ball Semiconductor Inc., Allen, TX (US)

( * ) Notice: Subject to any disclaimer, the term of this patent is extended or adjusted under 35 U.S.C. 154(b) by 431 days.

(21) Appl. No.: 11/529,531

(22) Filed: Sep. 29, 2006

(65) Prior Publication Data

US 2007/0084284 A1 Apr. 19, 2007

Related U.S. Application Data

(63) Continuation of application No. PCT/JP2005/006367, filed on Mar. 31, 2005.

(30) Foreign Application Priority Data

Mar. 31, 2004 (JP) ............................. 2004-108236

(51) Int. Cl.
*G01N 29/04* (2006.01)
(52) U.S. Cl. ........................ 73/24.01; 73/24.06; 73/584; 310/313 R; 310/313 A; 310/313 B
(58) Field of Classification Search ........................ None
See application file for complete search history.

(56) References Cited

FOREIGN PATENT DOCUMENTS

| JP | 3-115853 | 5/1991 |
|---|---|---|
| JP | 9-189685 | 7/1997 |
| JP | 2002-141769 | 5/2002 |

OTHER PUBLICATIONS

Yamanaka, K. et al., "Ball SAW Device for Hydrogen Gas Sensor", IEEE Ultrasonics Symposium, 2003, pp. 299-302.*
Ishikawa, S. et al., "Analysis of Spurious Bulk Waves in Ball Surface Wave Device", Ultrasonics, vol. 41, 2003, pp. 1-8.*

(Continued)

*Primary Examiner*—Daniel S Larkin

(57) ABSTRACT

An environment difference detector includes an elastic surface wave element equipped with a substrate including a surface having an annular surface acoustic wave circulating path, a surface acoustic wave exciting/receiving unit exciting a surface acoustic wave along the circular path and receiving the circulated surface acoustic wave, and a sensitive film disposed on the circular path to change an elastic nature in accordance with a change in an adjacent environment, a speed/intensity measuring unit measuring a circulating speed and intensity of the surface acoustic wave from an electric signal generated by the unit when the unit receives the circulating surface acoustic wave, and an environment evaluation unit evaluating an environment adjacent to the sensitive film from at least one of the circulating speed and the intensity measured by the unit.

13 Claims, 11 Drawing Sheets

OTHER PUBLICATIONS

Nakaso, N. et al., "Diffraction-Free Propagation of Collimated SAW Around a Quartz Ball", IEEE Ultrasonics Symposium, 2002, pp. 47-52.*

Yamanaka, K. et al., "Precise Velocity Measurement of Surface Acoustic Waves on a Bearing Ball", Applied Physics Letters, vol. 76, No. 19, May 8, 2000, pp. 2797-2799.*

International Preliminary Report on Patentability, mailed Oct. 26, 2006, and issued in corresponding International Patent Application No. PCT/JP2005/006367.

Satoru Ishikawa et al., "Sensitivity evaluation of the Ball SAW Hydrogen Gas Sensor", Technical Reports of IEICE, vol. 103, No. 340, Sep. 23, 2003, pp. 73-78.

Shingo Akao et al., "Observation of the Roundtrips of SAW on a Single Crystal $LiNbO_3$ Ball", Proceedings of Symposium on Ultrasonic Electronics, vol. 24, Nov. 12, 2003, pp. 221-222.

International Search Report dated Jul. 12, 2005 in corresponding PCT Patent Application No. PCT/JP2005/006367.

* cited by examiner

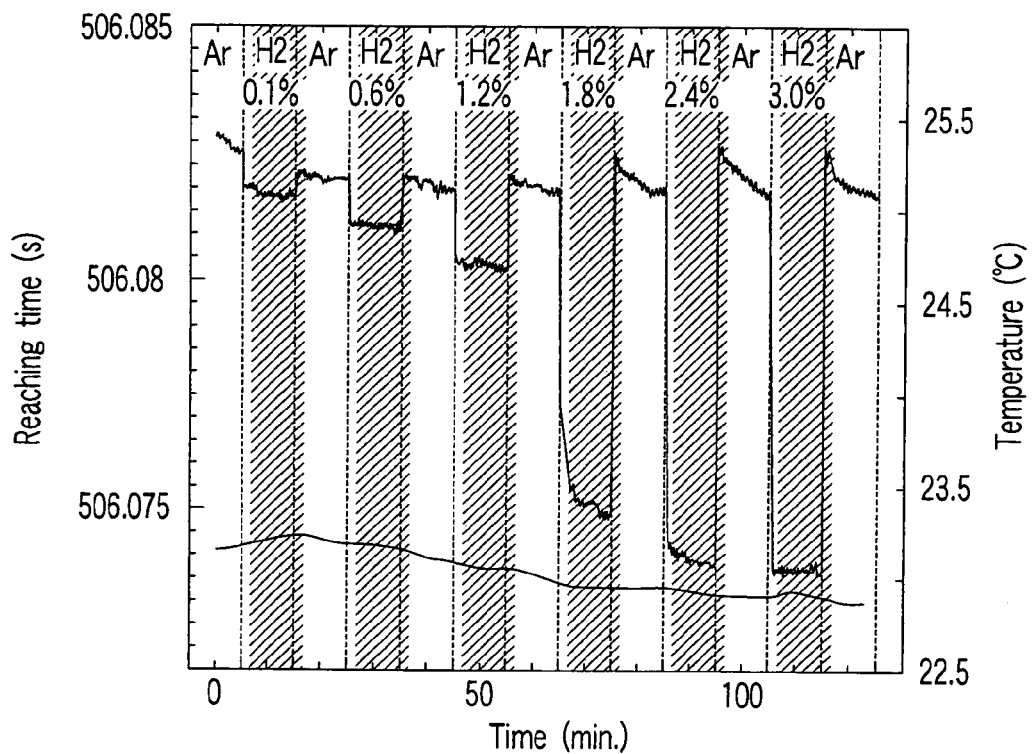
F I G. 4A
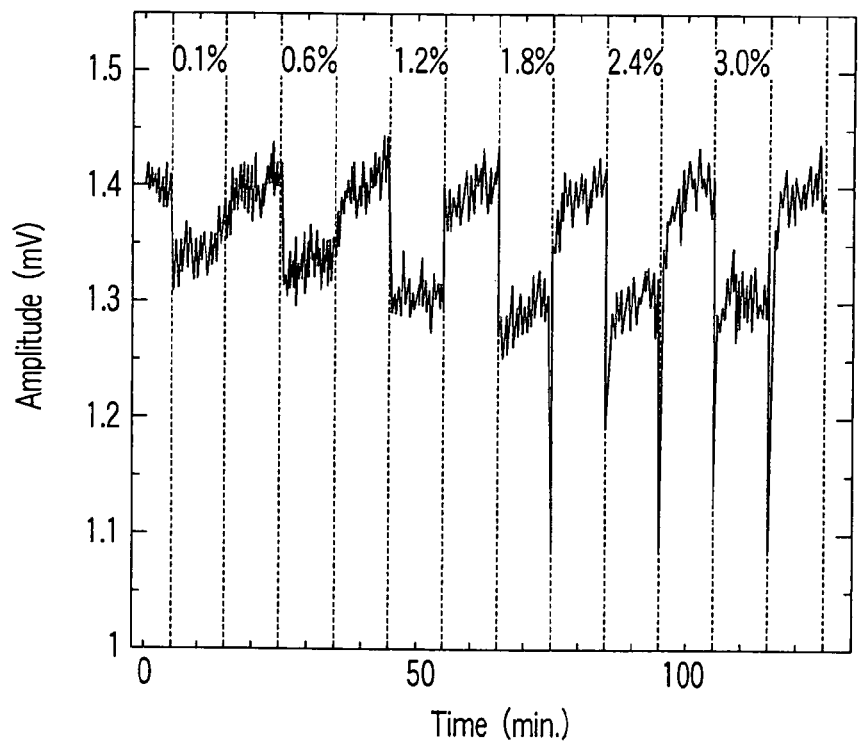
F I G. 4B

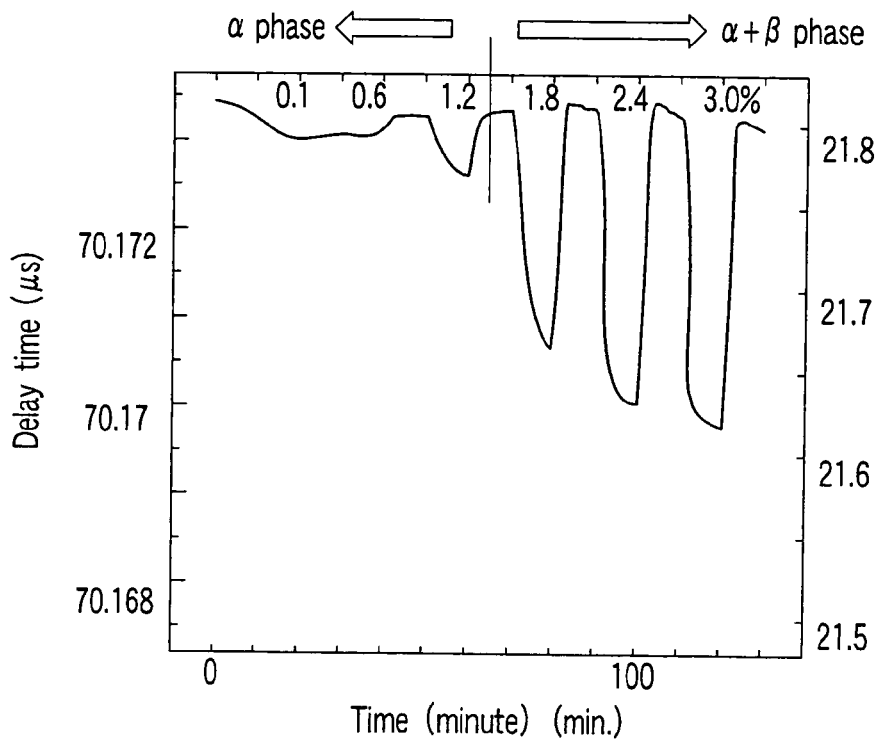
F I G. 6A
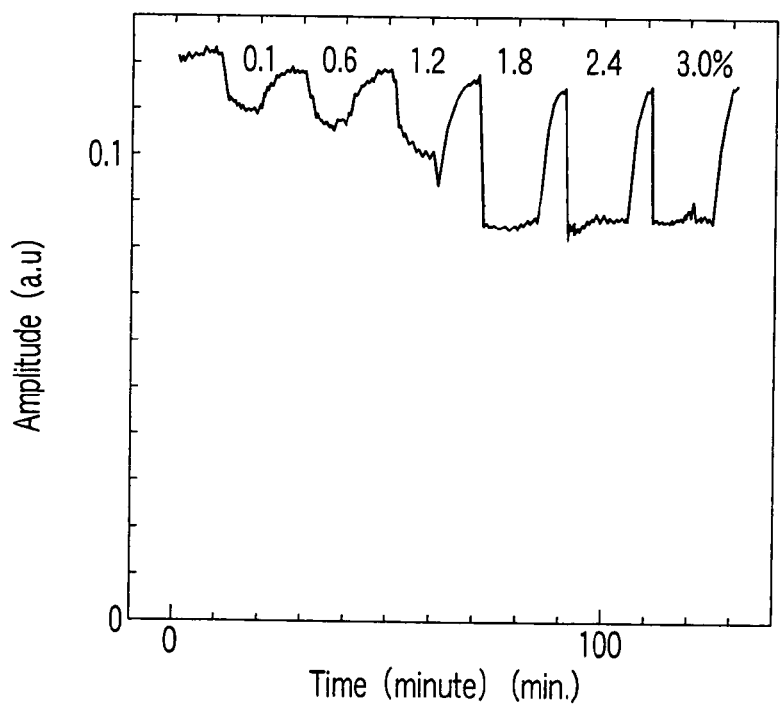
F I G. 6B

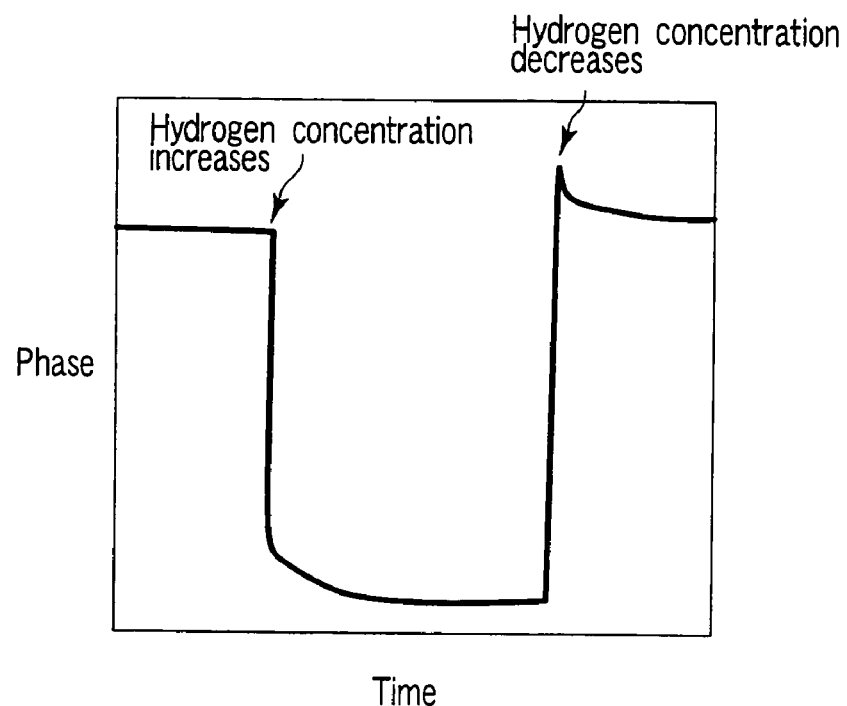
F I G. 7A
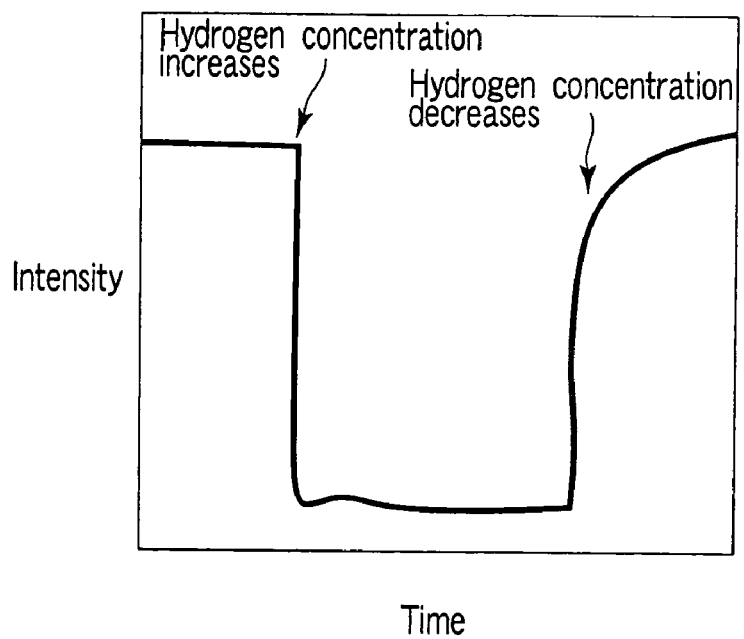
F I G. 7B

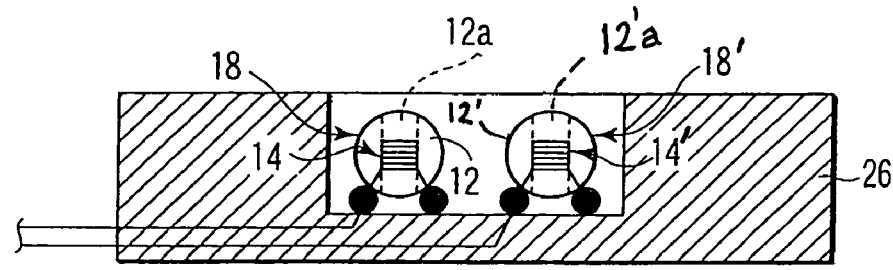
F I G. 10A
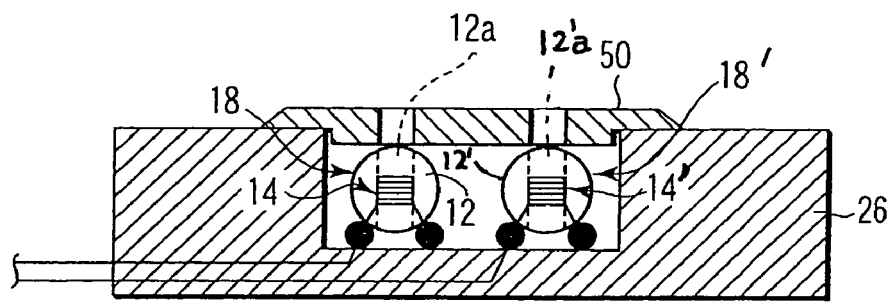
F I G. 10B
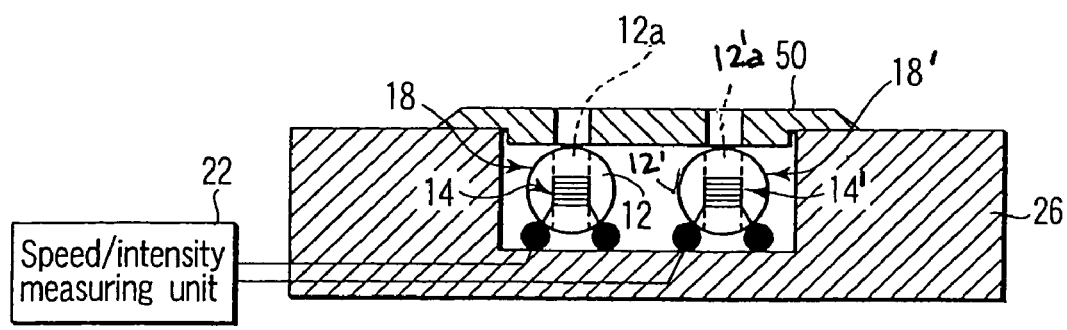
F I G. 10C

ENVIRONMENT DIFFERENCE DETECTOR

CROSS-REFERENCE TO RELATED APPLICATIONS

This is a Continuation Application of PCT Application No. PCT/JP2005/006367, filed Mar. 31, 2005, which was published under PCT Article 21(2) in Japanese.

This application is based upon and claims the benefit of priority from prior Japanese Patent Application No. 2004-108236, filed Mar. 31, 2004, the entire contents of which are incorporated herein by reference.

BACKGROUND OF THE INVENTION

1. Field of the Invention

The present invention relates to an environment difference detector for detecting an environment difference.

2. Description of the Related Art

Heretofore, various environment difference detectors for detecting environment differences have been known.

For example, to detect a difference of various gas components, which is an environment difference in an atmosphere, a vapor-phase chemical process or the like, various gas sensors such as a contact combustion type sensor, a semiconductor sensor, and an elastic surface wave sensor have conventionally been used as environment difference detectors. The conventional elastic surface wave sensor uses a planar elastic surface wave element, and thus it is generally said to be high in sensitivity.

For example, the planar elastic surface wave element used for the conventional elastic surface wave sensor includes a substrate made of a piezoelectric crystal such as rock crystal, lithium niobate ($LiNbO_3$), lithium tantalite ($LiTaO_3$), or the like, or a multilayered substrate in which an oxide film is formed on a silicon substrate or a glass substrate, and a piezoelectric thin film made of zinc oxide or aluminum nitride, and the like is further formed on the oxide film.

At two positions on a surface of the substrate separated from each other by a predetermined distance, two bamboo blind-shaped electrodes are arranged which function as a surface acoustic wave exciting unit and a surface acoustic wave receiving unit. Each of the two bamboo blind-shaped electrodes is made of a highly conductive metal such as aluminum or gold. The bamboo blind-shaped electrode as the surface acoustic wave exciting unit subjects a high-frequency signal supplied from a high frequency generating unit to piezoelectric conversion, and excites a surface acoustic wave on the surface of the substrate to propagate it on the surface. Then, the bamboo blind-shaped electrode as the surface acoustic wave receiving unit converts the surface acoustic wave excited and propagated on the surface of the substrate by the bamboo blind-shaped electrode as the surface acoustic wave exciting unit into a high-frequency signal again by piezoelectric conversion to supply it to a detection/output unit.

On the surface of the substrate, a sensitive film that reacts to a specific atom or molecule is additionally disposed between the two bamboo blind-shaped electrodes. This reaction includes for example adsorption or occlusion of the specific atom or molecule, and heat generation with respect to the specific atom or molecule. The sensitive film changes physical properties such as a propagation speed, an attenuation coefficient, a dispersed state, or the like of the elastic surface wave propagated between the two bamboo blind-shaped electrodes, in accordance with a degree of the reaction of the sensitive film to the specific atom or molecule. Accordingly, by measuring the above physical properties, it is possible to evaluate the degree of the reaction of the sensitive film to the specific atom or molecule, and furthermore a concentration of specific atoms or molecules in an environment adjacent to the sensitive film.

In the conventional planar elastic surface wave element configured in the above manner, as the elastic surface wave is diffused in a direction orthogonal to its propagating direction while it is propagated on the surface of the substrate, and there is a limit to a size of the substrate, a surface acoustic wave propagating distance to be set between the two bamboo blind-shaped electrodes is equal to or less than 10 mm. In order to detect an environment difference by using the conventional planar elastic surface wave element which can set only such a short surface acoustic wave propagating distance, a thickness of the sensitive film disposed between the two bamboo blind-shaped electrodes must be set to a certain size or more, e.g., 100 nm or more. However, when the thickness of the sensitive film becomes larger, an environment difference detection speed in the environment difference detector which uses the conventional planar elastic surface wave element becomes slow or the sensitive film is easily damaged.

The present invention has been made under the foregoing situation, and an object of the invention is to provide an environment difference detector which has a simple configuration, which is difficult to fail, which is low in manufacturing cost, and which can measures a desired environment difference quickly and highly accurately.

BRIEF SUMMARY OF THE INVENTION

In order to achieve the above described object of the invention, an environment difference detector according to the present invention comprises:

an elastic surface wave element equipped with a substrate including a surface having at least one annular and circular path along which a surface acoustic wave circulates, a surface acoustic wave exciting/receiving unit exciting a surface acoustic wave along the circular path and receiving the surface acoustic wave excited and circulated along the circular path, and a sensitive film disposed on at least one part of the circular path to change an elastic nature in accordance with a change in an adjacent environment;

a speed/intensity measuring unit measuring a circulating speed and intensity of the surface acoustic wave from an electric signal generated by the surface acoustic wave exciting/receiving unit when the surface acoustic wave exciting/receiving unit receives the surface acoustic wave circulating along the circular path; and an environment evaluation unit evaluating an environment adjacent to the sensitive film from at least one of the circulating speed and the intensity measured by the speed/intensity measuring unit.

The environment difference detector according to the invention configured as described above uses the elastic surface wave element equipped with the substrate including the surface having at least one annular and circular path along which the surface acoustic wave circulates, the surface acoustic wave exciting/receiving unit exciting the surface acoustic wave along the circular path and receiving the surface acoustic wave excited and circulated along the circular path, and the sensitive film disposed on at least one part of the circular path to change the elastic nature in accordance with the change in the adjacent environment. Thus, by repeatedly circulating the surface acoustic wave excited by the surface acoustic wave exciting/receiving unit along the circular path of the surface of the substrate, the propagation distance of the surface acoustic wave can be set much longer as compared with the case of using the conventional planar elastic surface wave element. As a result, even when a thickness of the sensitive film disposed on the at least one part of the circular path is set small, a desired environment difference can be quickly and highly accurately measured. Further, the configuration of the environment difference detector is simple, and a failure is difficult to occur in that environment difference detector.

Recently, various attempts have been made to promote use of hydrogen as a clean fuel. For this purpose, for example, a hydrogen sensor is required, which can highly and accurately detect leakage of hydrogen from a fuel cell or a concentration of hydrogen to be used within a time as short as possible. The inventors of this invention have discovered that propagation characteristics of the surface acoustic wave are different in propagation speed of the surface acoustic wave and in response to the change of signal intensity, in accordance with a change in a hydrogen absorbing/discharging process or in a hydrogen concentration range when a hydrogen gas is detected by using a hydrogen absorption or adsorption phenomenon of a palladium thin film. And, the inventors have further discovered that, by using the elastic surface wave element including the surface having the at least annular and circular path along which the surface acoustic wave circulates, the hydrogen sensor with higher performance can be obtained.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently embodiments of the invention, and together with the general description given above and the detailed description of the embodiments given below, serve to explain the principles of the invention.

FIG. 4A shows an experiment result of a change in a reaching time of the surface acoustic wave (corresponding to a circulating speed, a delay time, and a phase) when a concentration of the hydrogen gas added in the argon gas is gradually increased from 0.13% to 3% in the experiment of FIG. 3B.

FIG. 4B shows an experiment result of a change in an intensity of the surface acoustic wave when the concentration of the hydrogen gas added in the argon gas is gradually increased from 0.13% to 3% in the experiment of FIG. 3B.

FIG. 6A shows a result of an experiment performed under the same conditions as those of the experiment whose result is shown in FIG. 4A by another yardstick.

FIG. 6B shows a result of an experiment performed under the same conditions as those of the experiment whose result is shown in FIG. 4B.

FIG. 7A shows a change in a phase of the electric signal corresponding to the surface acoustic wave when the hydrogen concentration increases and decreases in a hydrogen concentration area between 1.2% and 1.8%.

FIG. 7B shows a change in an intensity of the electric signal corresponding to the surface acoustic wave when the hydrogen concentration increases and decreases in the hydrogen concentration area between 1.2% and 1.8%.

FIG. 10A is a figure showing a section of a first step of a manufacturing method for an elastic surface wave element unit used in a concrete example of the environment difference detector according to the embodiment of the present invention, the elastic surface wave element unit being incorporated with two elastic surface wave elements for hydrogen concentration measurement and for a temperature calibration.

FIG. 10B is a figure showing a section of a second step of a manufacturing method for an elastic surface wave element unit used in a concrete example of the environment difference detector according to the embodiment of the present invention, the elastic surface wave element unit being incorporated with two elastic surface wave elements for hydrogen concentration measurement and for a temperature calibration.

FIG. 10C is a figure showing a section of a third step of a manufacturing method for an elastic surface wave element unit used in a concrete example of the environment difference detector according to the embodiment of the present invention, the elastic surface wave element unit being incorporated with two elastic surface wave elements for hydrogen concentration measurement and for a temperature calibration.

DETAILED DESCRIPTION OF THE INVENTION

Figure 1:
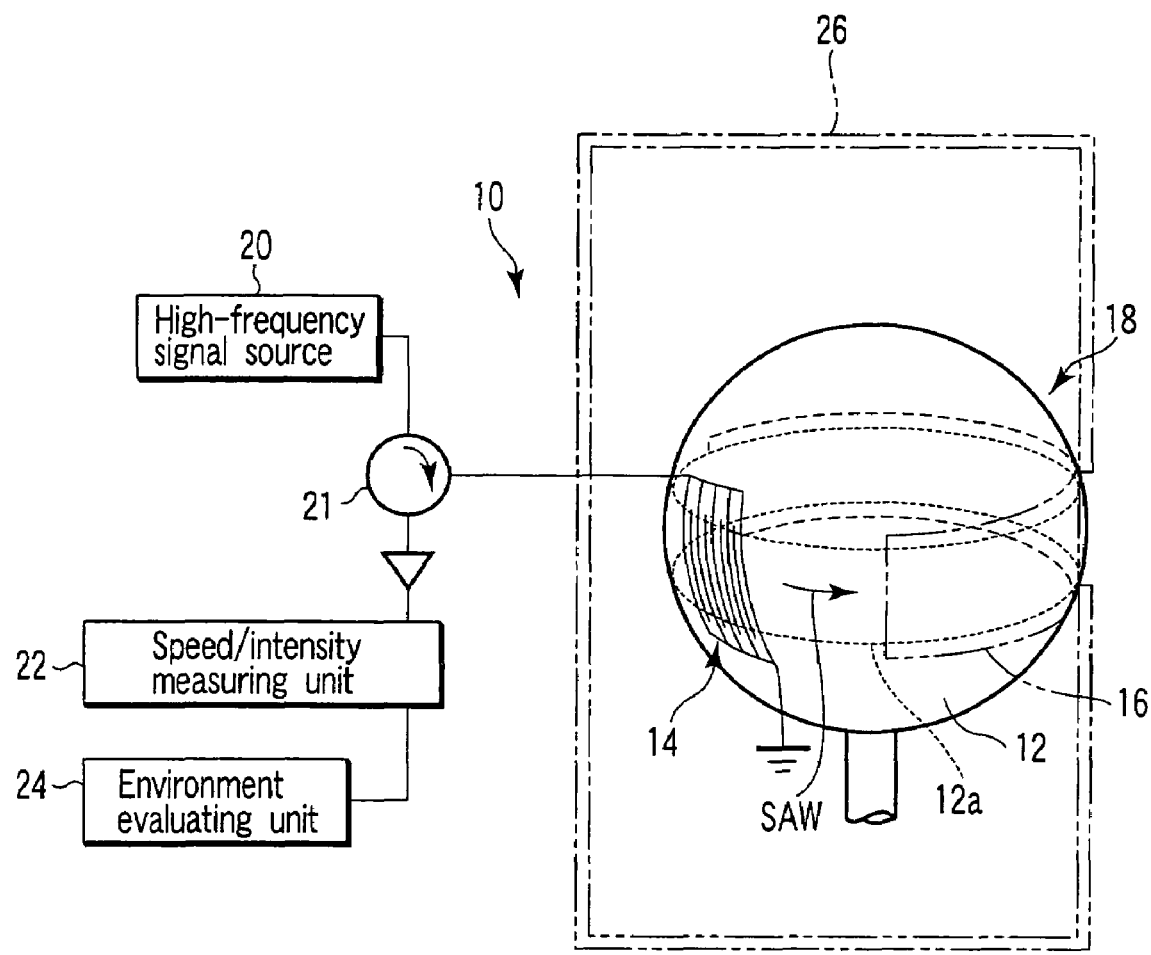
FIG. 1 is a figure schematically showing an entire configuration of an environment difference detector according to one embodiment of the present invention.

First, with reference to FIG. 1, an environment difference detector 10 according to an embodiment of the present invention will be described. FIG. 1 schematically shows an entire configuration of the environment difference detector 10 according to the embodiment of the present invention.

The environment difference detector 10 uses an elastic surface wave element 18 equipped with a substrate 12 including a surface having at least one annular and circular path 12a along which a surface acoustic wave SAW circulates, a surface acoustic wave exciting/receiving unit 14 exciting a surface acoustic wave SAW along the circular path 12a and receiving the surface acoustic wave SAW excited and circulated along the circular path 12a, and a sensitive film 16 disposed on at least one part of the circular path 12a to change an elastic nature in accordance with a change in an adjacent environment.

The surface acoustic wave includes all elastic waves concentrating energy along a surface of the substrate and propagating along the surface. Further, the surface acoustic wave includes for example a wave propagating with leaking some energy into the substrate such as pseudo Sezawa wave, SH wave, Love wave capable of propagating in a film disposed on the surface, or a corridor wave.

The substrate 12 can be made of a material capable of exciting and propagating a surface acoustic wave SAW along its surface, or by covering a surface of a material incapable of exciting and propagating a surface acoustic wave SAW with a film of a material capable of exciting and propagating a surface acoustic wave SAW.

As the material of the substrate 12 capable of exciting and propagating the surface acoustic wave SAW on its surface, a single crystal such as rock crystal, lithium niobate ($LiNbO_3$) or lithium tantalite ($LiTaO_3$) is known. Besides, it is known that a predetermined circular path 12a can be set around a crystal axis on a surface of such a material. More specifically, when such a material is shaped into a sphere to be presumed as the Earth and its crystal axis is presumed to be an earth's axis, the circular path 12a can be set along a line equivalent to the equator on a surface of the spherical shape.

When the substrate 12 is made of a material such as a glass incapable of exciting and propagating a surface acoustic wave SAW and its surface is covered with a film of a piezoelectric material capable of exciting a surface acoustic wave SAW, a surface acoustic wave SAW can be excited and propagated along an annular area including a maximum circumferential line on the surface and extending in a desired direction, as a circular path. This means that a desired number of circular paths can be set on the surface of one substrate 12 configured as described above.

It has been known that the surface acoustic wave SAW can be circulated repeatedly along a predetermined circular path by exciting the surface acoustic wave SAW along the surface of the spherical substrate, the surface being capable of exciting and propagating a surface acoustic wave SAW, under predetermined conditions, from a document prepared by one of the inventors of the present invention, Yamanaka, and et al. and published in 2000 (K. Yamanaka, H. Cho and Y. Tsukahara; Technical Report of Institute of Electronics, Information and Communication Engineers; US 2000-14 (2000) 49.). According to this document, the predetermined conditions are to properly select a frequency of a surface acoustic wave SAW excited along the circular path and a size (that is, a width) of the surface acoustic wave SAW in a direction orthogonal to a propagating direction along the circular path in connection with a diameter of the circular path. It is known that when a surface acoustic wave SAW is excited under predetermined conditions along a predetermined circular path on a rock crystal ball having a diameter of 10 mm, the number of circulating times of the surface acoustic wave SAW along the circular path is 300 to 500. This means that even when a spherical elastic surface wave element using a substrate having a diameter of 1 mm is used, a propagating distance of 900 mm at 300 circulating times can be obtained. In this case, as compared with the conventional planar elastic surface wave element in which a surface acoustic wave propagating distance can be obtained only for 1 mm to 10 mm, a propagating distance is longer by one to two digits, and resolution can be improved (sensitivity is improved) by one to two digits in measurement of propagation time.

In this embodiment, the entire surface of the substrate 12 is a sphere. However, a part of the surface excluding at least the annular and circular path 12a along which the surface acoustic wave SAW circulates (i.e., a part along which the surface acoustic wave SAW does not circulates) may be shaped into any shape. And, the substrate 12 is supported on a base (not shown) at this part.

The surface acoustic wave exciting/receiving unit 14 includes for example a bamboo blind-shaped electrode, and is connected to a high-frequency signal source 20 for exciting a surface acoustic wave SAW along the circular path 12a on the surface of the substrate 12 via a circulator 21.

The surface acoustic wave exciting/receiving unit 14 is further connected to a speed/intensity measuring unit 22 which measures a circulating speed and intensity of the surface acoustic wave SAW from an electric signal generated by the surface acoustic wave exciting/receiving unit 14 when it receives the surface acoustic wave SAW circulating along the circular path 12a. In this embodiment, the speed/intensity measuring unit 22 includes an oscilloscope connected to the circulator 21. In this case, a change in the circulating speed can be known by a change in phase shifting degree (delay time) when the electric signal generated by the surface acoustic wave exciting/receiving unit 14 at a time that it receives the surface acoustic wave SAW circulating along the circular path 12a is seen on the oscilloscope.

The speed/intensity measuring unit 22 is further connected to an environment evaluating unit 24 which evaluates an environment adjacent to the sensitive film 12a from at least one or both of the circulating speed and intensity of the surface acoustic wave SAW measured by the speed/intensity measuring unit 22.

The surface acoustic wave exciting/receiving unit 14 can be directly disposed on the circular path 12a of the surface of the substrate 12, or arranged to face the circular path 12a with a predetermined gap therebetween. When the surface acoustic wave exciting/receiving unit 14 is directly disposed on the circular path 12a, it is preferable that the surface acoustic wave exciting/receiving unit 14 is made of a material such as a gold or aluminum which makes a mass of the surface acoustic wave exciting/receiving unit 14 as small as possible, to be thinned as much as possible.

The surface acoustic wave exciting/receiving unit 14 can include an exciting-only part and a receiving-only part with respect to one corresponding circular path 12a. In this case, as compared with a case in which the unit 14 is used for both exciting a surface acoustic wave and receiving the surface acoustic wave, an electric circuit for driving the exciting-only part and an electric circuit driven by the receiving-only part can be configured independently of each other so that an entire configuration of all electric circuits for the surface acoustic wave exciting/receiving unit 14 can be simplified.

The change of the sensitive film 16 caused in response to the change in the adjacent environment includes adsorption, occlusion, and chemical reaction of specific atoms or molecules.

In the present invention, the environment evaluation of the environment to be measured does not need to be executed in real time. In other words, the environment difference detector 10, especially the elastic surface wave element 18, is placed in an environment to be measured, and the environment difference detector 10, especially the elastic surface wave element 18, is removed after the sensitive film 16 of the elastic surface wave element 18 is operated by the environment to be measured. Then, the environment to be measured is evaluated from the removed elastic surface wave element 18 by the environment evaluating unit 24 via the high-frequency signal source 20, the circulator 21, and the speed/intensity measuring unit 22.

The circulating speed of the surface acoustic wave SAW can be measured on a basis of a delay time to a predetermined propagating time which is needed for a predetermined number of circulating times, a phase shifting from a predetermined frequency in the predetermined number of circulating times, or the like. And, the intensity of the surface acoustic wave SAW can be measured on a basis of an attenuation rate of the intensity of the surface acoustic wave SAW while it circulates.

In the elastic surface wave element 18, the surface acoustic wave SAW excited and propagated along the circular path 12a on the surface of the substrate 12 by the surface acoustic wave exciting/receiving unit 14 is repeatedly circulated along the circular path 12a a number of times as described above. Thus, the propagation distance of the surface acoustic wave SAW can be increased by one to two digits as compared with the conventional planar elastic surface wave element, and a resolution in measurement of the propagating time can be improved (sensitivity can be improved) by one to two digits. Accordingly, even when the sensitive film 16 is formed thinner as compared with the conventional case, an evaluation accuracy of the change in the environment adjacent to the sensitive film 16 evaluated through the sensitive film 16 is not reduced, and the thickness of the sensitive film 16 which is smaller than the conventional case increases a speed for detecting the environmental change (environment difference detecting speed) with eliminating a possibility of damaging the sensitive film.

The elastic surface wave element used in the environment difference detector according to the present invention, e.g., the elastic surface wave element 18 used in the environment difference detector 10 shown in FIG. 1, can include a protective container 26 for housing the elastic surface wave element 18 while exposing the sensitive film 16 to the outside. By housing the elastic surface wave element 18 in the protective container 26, the elastic surface wave element 18 can be easily protected from an external force, and can be easily distributed in a market.

The elastic surface wave element 18 equipped with the surface acoustic wave exciting/receiving unit 14 is housed in the protective container 26 before the sensitive film 16 is disposed. After exciting and circulating of a surface acoustic wave SAW along the circular path 12a by the surface acoustic wave exciting/receiving unit 14 is checked, the sensitive film 16 can be disposed on at least one part of the circular path 12a of the substrate 12 housed in the protective container 26, from the outside of the protective container 26. If the sensitive film 16 can be formed by deposition, it is preferable because its formation is facilitated.

In the elastic surface wave element used in the environment difference detector according to the present invention, more precisely, even a change in temperature which is a kind of environment causes a slight change in the circulating speed or intensity of the surface acoustic wave SAW. This occurs because physical properties of the substrate material or the sensitive film material slightly change, or the diameter of the annular and circular path slightly changes due to a temperature influence. Thus, when a difference of an environment other than the temperature is detected by the environment difference detector according to the present invention, the influence of the temperature change must be taken into consideration.

To take the temperature influence into consideration, in the environment difference detector according to the present invention, two identical elastic surface elements are used, or at least two circular paths are disposed on a surface of a substrate of one elastic surface wave element and a surface acoustic wave exciting/receiving unit is disposed on each of the two circular paths.

In the former case which uses the two identical elastic surface wave elements, only one elastic surface wave element is placed in an environment to detect a difference of the environment, and the other elastic surface wave element is shielded from the environment excepting a temperature and only the temperature of the environment is accurately conducted to the circular path. Then, a change in the circulating speed or intensity of the surface acoustic wave measured by the other elastic surface wave element only under the influence of the temperature change in the environment is reflected on a change in the circulating speed or intensity of the surface acoustic wave measured by the one elastic surface wave element under the influence of not only the temperature change of the environment but also another desired change in the environment.

In the latter case, where the at least two circular paths 12a and 12"a are disposed on the surface of the substrate 12 of one elastic surface wave element 18", and the surface acoustic wave exciting/receiving unit 5, 14 and 14" are disposed on the two circular paths 12 and 12"a, only one circular path 12a is placed in an environment whose difference is to be detected, and the other circular path 12"a is shielded from the environment excepting a temperature and only the temperature of the environment is accurately conducted to the other circular path 12"a. Then, a change in the circulating speed or intensity of the surface acoustic wave measured by the other circular path 12"a only under the influence of the temperature change in the environment is reflected on a change in the circulating speed or intensity of the surface acoustic wave measured by the one circular path 12a under the influence of not only the temperature change of the environment but also another desired change in the environment.

Figure 2:
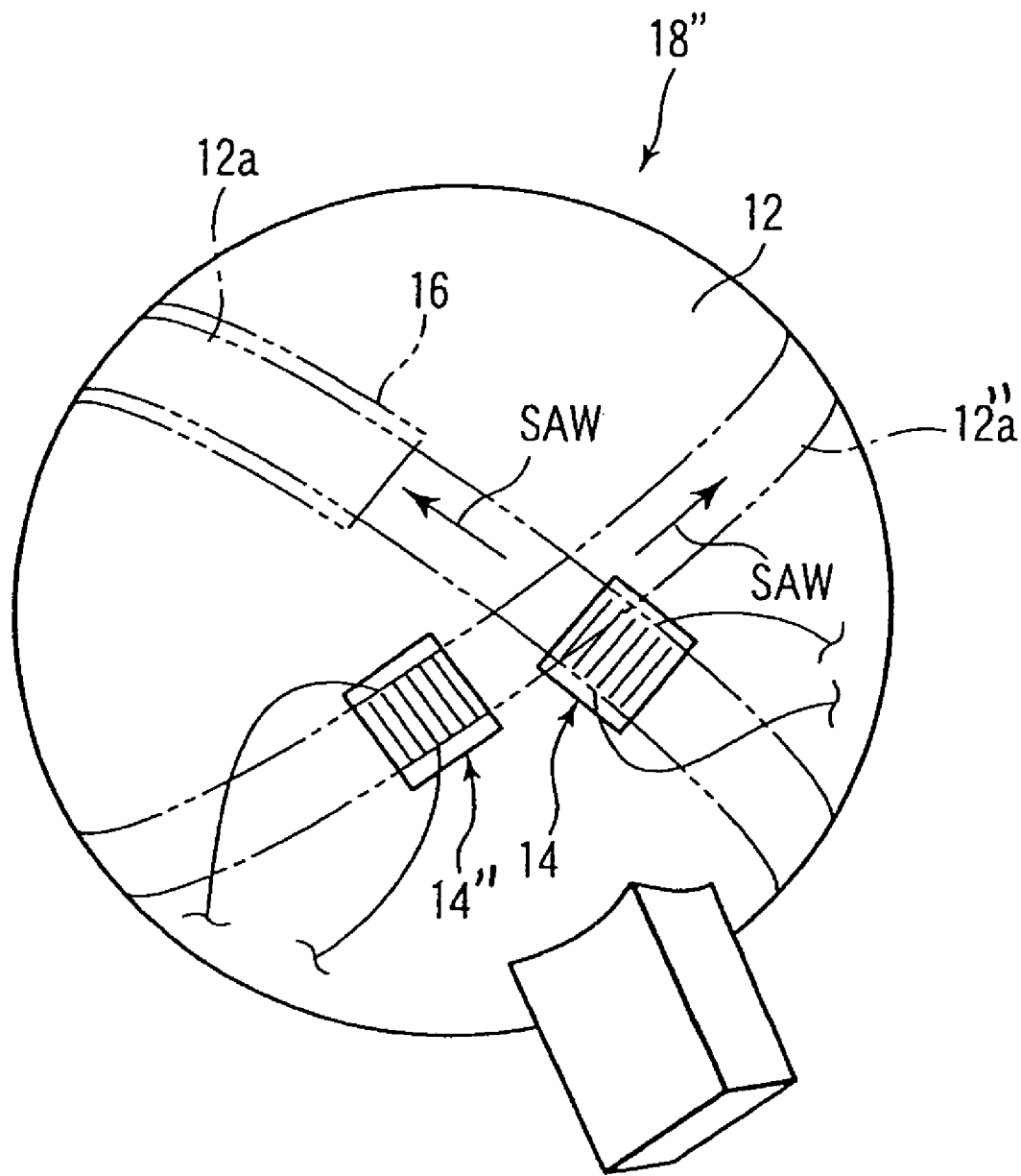
FIG. 2 is a figure schematically showing a modification of an elastic surface wave element of the environment difference detector of the embodiment of the present invention.

A modification of one elastic surface wave element used in, the latter case is schematically shown in FIG. 2. In an elastic surface wave element 18" of the modification, structural elements similar to those of the elastic surface wave element 18 shown in FIG. 1 are denoted by reference numerals similar to those denoting corresponding structural elements of the elastic surface wave element 18 of FIG. 1, and detailed description thereof will be omitted.

A modification of one elastic surface wave element used in the latter case is schematically shown in FIG. 2. In an elastic surface wave element 18" of the modification, structural elements similar to those of the elastic surface wave element 18 shown in FIG. 1 are denoted by reference numerals similar to those denoting corresponding structural elements of the elastic surface wave element 18 of FIG. 1, and detailed description thereof will be omitted.

Further, in the environment difference detector according to the present invention, by measuring only one of the circulating speed and the intensity of the surface acoustic wave propagating along the circular path on the surface of the elastic surface element, a desired change in an environment adjacent to the circular path can be evaluated. Alternatively, by measuring both of the circulating speed and the intensity of the surface acoustic wave propagating along the circular path on the surface of the elastic surface wave element and by comparing the changes of the same environment evaluated from the measuring results of the both of them, it is possible to increase an accuracy of the measuring result of the environment change.

When the sensitive film 16 is brought into contact with a specific gas, the sensitive film 16 can change propagation characteristics of the surface acoustic wave SAW propagating along the circular path 12a. In this case, the sensitive film 16 may adsorb the specific gas in its surface to make the propagating speed of the surface acoustic wave propagating along the circular path 12a slow or to reduce its intensity by an effect of a mass of the adsorbed specific gas.

A material of the sensitive film 16 preferably reacts to a specific gas alone and further makes a reversible reaction.

As such a sensitive film, for example, palladium which occludes hydrogen and changes into a hydrogen alloy thereby changing its mechanical strength, platinum which has a high adsorptivity to ammonium, tungsten oxide which adsorbs a hydrogen compound, or phthalocyannine which selectively adsorbs carbon monoxide, carbon dioxide, sulfur dioxide, nitrogen dioxide or the like are known.

Figure 3A:
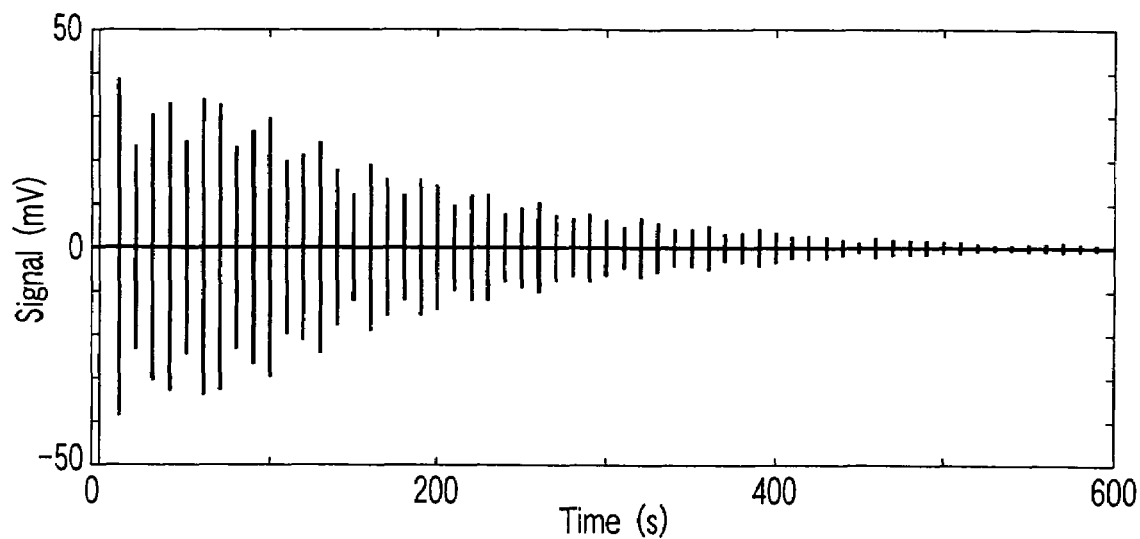
FIG. 3A is a diagram showing high-frequency signals with a lapse of time, each high-frequency signal corresponding to a surface acoustic wave received by a surface acoustic wave exciting/receiving unit on an annular and circular pass of a substrate of the elastic surface wave element of the environment difference detector of FIG. 1 at every circulation of the surface acoustic wave along the circular pass after a high-frequency signal is applied on the circular pass by the surface acoustic wave exciting/receiving unit and the surface acoustic wave is excited by the applied high-frequency signal and propagates along the circular pass, the substrate being made of rock crystal in a diameter of 10 mm, the circular pass being provided with a sensitive film for hydrogen made of palladium by deposition with a length of about 6 mm in the extending direction of the circular path and a thickness of 20 nm, the elastic surface wave element being disposed in an environment with keeping a room temperature and being filled with an argon gas to 100%, and the high-frequency signal being applied to the circular pass by the surface acoustic wave exciting/receiving unit at 45 MHz.
Figure 3B:
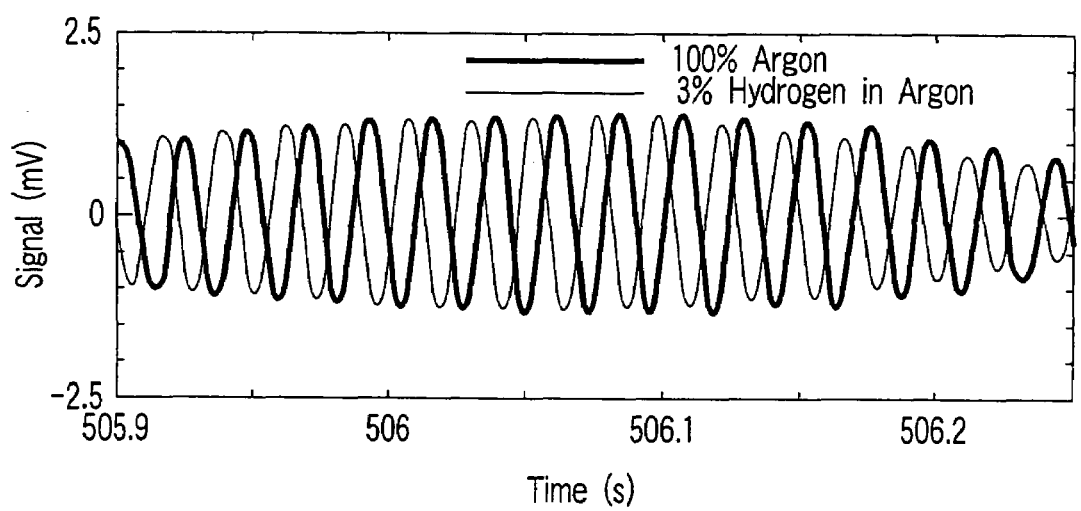
FIG. 3B shows a high-frequency signal, which corresponds to the surface acoustic wave at 51st circulation (around 400 μsec) while the surface acoustic wave circulates along the circular path of the rock crystal substrate with the diameter of 10 mm in the environment being kept at a room temperature and being filled with an argon gas to 100%, by a thick solid line, and further shows a high-frequency signal, which corresponds to the surface acoustic wave at 51st circulation (around 400 μsec.) while the surface acoustic wave circulates along the circular path of the rock crystal substrate with the diameter of 10 mm in the environment being kept at a room temperature and being filled with an argon gas and a hydrogen gas added in the argon gas to 3%.

FIGS. 3A and 3B show experimental results when the environment difference detector 10 shown in FIG. 1 is manufactured and experimented under conditions described below.

That is, the substrate 12 is made of rock crystal with a diameter of 10 mm, and a surface acoustic wave exciting/receiving unit 14 is disposed to correspond to the annular and circular path 12a of the substrate 12. Then, the sensitive film 16 is formed by deposition on the annular and circular path 12a of the substrate 12 by palladium with a length of about 6 mm in the extending direction of the circular path 12a and a thickness of 20 nm.

Since the palladium selectively absorbs hydrogen only and forms a hydrogen alloy, it provides a hydrogen sensor having high selectivity.

FIG. 3A shows high-frequency signals with a lapse of time, each of which corresponds to the surface acoustic wave SAW at every one circulation received by the surface acoustic wave exciting/receiving unit 14, after an RF burst signal of 45 MHz is applied on the circular path 12a by the surface acoustic wave exciting/receiving unit 14 to excite and propagate the surface acoustic wave SAW along the circular path 12a in an environment which has a room temperature and which is filled with an argon gas of 100%. In this case, a circulating time of the surface acoustic wave SAW needed for one circulation along the circular path 12a on the rock crystal substrate 12a having the diameter of 10 mm is about 10 µsec.

FIG. 3B shows the high-frequency signal indicated by a thick solid line and corresponding to the surface acoustic wave SAW at the 51st circulation (around 400 µsec.) while the surface acoustic wave SAW circulates along the circular path 12a on the rock crystal substrate 12a having the diameter of 10 mm as described above in the environment which has the room temperature and which is filled with argon gas of 100%, and the high-frequency signal indicated by a thin solid line and corresponding to the surface acoustic wave SAW at the 51st circulation (around 400 µsec.) while the surface acoustic wave SAW circulates along the circular path 12a on the rock crystal substrate having the diameter of 10 mm as described above in the environment which has the room temperature and which is filled with argon gas to which hydrogen gas is added by 3%.

Since the palladium absorbs hydrogen and forms a hydrogen absorbed alloy thereby becoming mechanically hard, the propagating speed of the surface acoustic wave SAW becomes faster. And, a reduction of the delay time (phase shifting) of the surface acoustic wave SAW measured at the 51st circulation in the environment which is filled with argon gas to which hydrogen gas is added by 3% with respect to the delay time (phase shifting) of the surface acoustic wave SAW measured at the 51st circulation in the environment which is filled with argon gas of 100% is about 3 nsec (about 7 ppm).

FIG. 4A shows a change in the delay time (phase shifting) indicating a change in the circulating speed of the surface acoustic wave at the 51st circulation (around 400 µsec.) while the surface acoustic wave SAW circulates along the circular path 12a on the rock crystal substrate 12a having the diameter of 10 mm as described above, when the concentration of the hydrogen gas added to the argon gas is gradually increased from 0.13% to 3% in the experiment of FIG. 3B.

FIG. 4B shows a change in the intensity of the electric signal corresponding to the surface acoustic wave SAW at the 51st circulation (around 400 µsec.) while the surface acoustic wave SAW circulates along the circular path 12a on the rock crystal substrate 12a having the diameter of 10 mm as described above, when the concentration of the hydrogen gas added to the argon gas is gradually increased from 0.13% to 3% in the experiment of FIG. 3B.

It is obvious from the experimental results shown in FIGS. 4A and 4B that reflections in the change (corresponding to a shift of the reaching time, a shift of the delay time, and a shift of the phase) and in the intensity (attenuation) are discontinuously different between a case in which a hydrogen concentration is 1.2% or less and a case in which a hydrogen concentration is 1.8% or more. This is because an area of an alpha-phase alone is present in the palladium sensitive layer 16 when the hydrogen concentration is 1.2% or less, and the palladium sensitive layer 16 starts to change from the alpha-phase to a beta-phase when the hydrogen concentration becomes more than 1.2%.

And, when the hydrogen concentration is higher than 1.8%, the intensity changes little. In this case, it is found that a change of hydrogen cannot be evaluated so accurately from the intensity alone.

The circulating speed and the intensity of the surface acoustic wave SAW at the predetermined circulation are affected by, in addition to the temperature and the hydrogen concentration of the environment adjacent to the surface acoustic wave exciting/receiving unit 14, a state of the surface acoustic wave exciting/receiving unit and sticking of, e.g., high molecules in air other than the hydrogen gas to the circular path 12a. Accordingly, when the circulating speed or the intensity of the surface acoustic wave SAW cannot be accurately measured at the predetermined circulation due to a large noise component caused by such an adverse effect, an element or a path for correction is necessary.

If the intensity is measured by digitization and analysis using Fourier transformation or the like, the circulating speed and the intensity can be measured more accurately. According to the method for measuring the circulating speed and the intensity of the surface acoustic wave, which uses Fourier transformation, a change of the electric signal corresponding to the circulating surface acoustic wave SAW with a lapse of time is digitized by using a digital oscilloscope as an oscilloscope used in the speed/intensity measuring unit 22 of FIG. 1 or a digitizer in the speed/intensity measurement unit 22. For example, a signal of 45 MHz at a first circulation is subjected to a frequency analysis, and its phase and intensity can be obtained by Fourier transformation (actually FFT processing). In this case, even when a noise is mixed in a specific frequency component, as the specific frequency component is obtained by integrating all the frequency components until then, a phase and intensity of the specific frequency component can be exactly obtained.

Alternatively, by applying wavelet conversion which uses Gabor function excellent in time/frequency resolution as a mother wavelet, the phase and the intensity of the specific frequency component can be obtained more exactly. For example, time in which a real part of wavelet conversion for a waveform of the specific frequency component of the electric signal at the 51st circulation is maximum is obtained, and this is set as a delay time. In this case, any one of the delay time and the phase can be used because each of them represented physically equally the circulating speed of the surface acoustic wave propagating along the circular path. Then, for example, the real part of the wavelet conversion which is maximum for the waveform of the specific frequency component of the electric signal at the 51st circulation becomes an intensity for the waveform of the specific frequency component.

Sampling time is 0.5 ns when the electric signal of the specific frequency component is actually measured. According to the wavelet analysis, however, complementation can be done at a time interval of 0.025 ns, so that the change of the electric signal can be observed by a resolution of 0.025 ns.

Thus, the method for obtaining the phase and the intensity of the specific frequency component by using Fourier transformation or wavelet conversion is influenced little by a noise which enters the electric signal corresponding to the specific frequency component from the actual electric circuit or the surroundings of the environment difference detector according to the invention.

Figure 5:
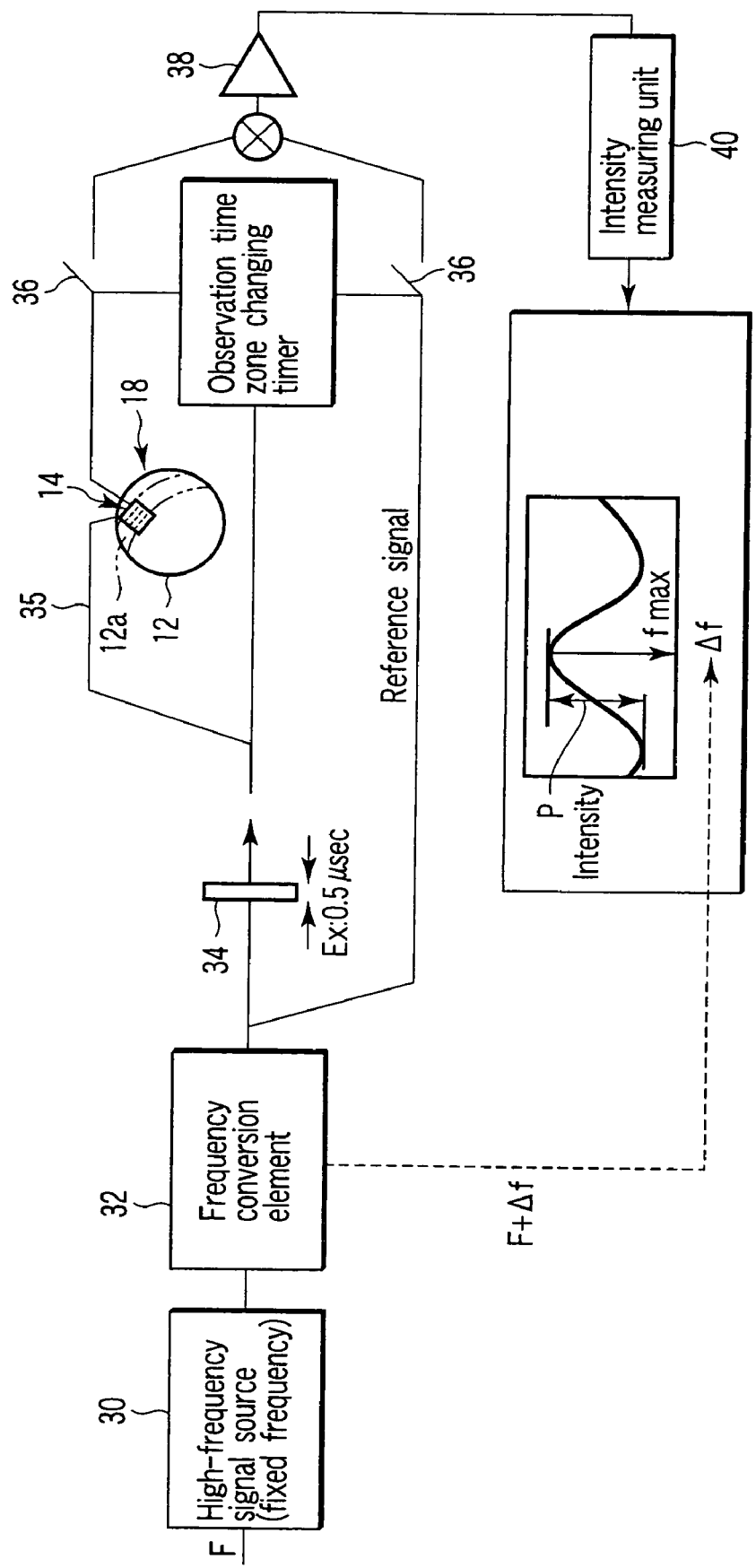
FIG. 5 is a figure schematically showing an electric circuit used for a signal processing method which uses an interference with a reference signal for measuring a phase (corresponding to the circulating speed) of a specific frequency component.

For measuring the phase of the specific frequency component, a method which uses an interference with a reference signal may be employed. FIG. 5 schematically shows an electric circuit which is used for this signal processing method. This electric circuit includes a high-frequency signal source 30 having a fixed frequency, and a frequency conversion element 32 having a modulation circuit for slightly modulating this fixed frequency. A high-frequency signal modulated by the frequency conversion element 32 cut out into a high-frequency burst signal of short time by a gate circuit 34, and then selectively added to the surface acoustic wave exciting/receiving unit 14 of the elastic surface wave element 18 via a switch 34 to excite and propagate a surface acoustic wave SAW along the circular path 12a on the substrate 12 of the elastic surface wave element 18. Only an electric signal at a predetermined designated number of circulating times among electric signal output at every circulation of the surface acoustic wave SAW along the circular path 12a on the substrate 12 of the elastic surface wave element 18 is cut out by a switch 36, and the electric signal at the predetermined designated number of circulating times is interfered with a reference signal from the frequency conversion element 32. The interfered electric signal is sent to an intensity measuring unit 40 via an amplifier 38, and an intensity P is measured by the intensity measuring unit 40. The intensity P to be measured here indicates a vibration when a frequency amount $\Delta f$ to be modulated by the frequency conversion element 32 is indicated along an abscissa. For example, a frequency in which the vibration intensity P is the maximum is employed as a parameter indicating a circulating speed of the surface acoustic wave SAW at the predetermined designated number of circulating times.

When the frequency of the maximum vibration intensity becomes great by 3 ppm due to the change in the environment adjacent to the elastic surface wave element 18 and the change in the physical nature of the sensitive film 16 on the circular path 12a of the substrate 12 of the elastic surface wave element 18, it can be approximately said that the circulating speed of the surface acoustic wave SAW circulating along the circular path 12a becomes faster by 3 ppm. When the change of the circulating speed is represented by the delay time, it can also be said that the delay time in relation to the circulation becomes shorter by 3 ppm. When the change of the circulating speed is represented by the phase, it is needless to say that a value obtained by dividing a total time T from a start of the circulation of the surface acoustic wave SAW to a point of time when an electric signal corresponding to the surface acoustic wave SAW at the predetermined designated number of circulating times is detected, by a cycle of the circulating surface acoustic wave SAW and further by multiplying the result from the division by a $2\pi$ radian corresponds to the phase of the electric signal corresponding to the surface acoustic wave SAW at the predetermined designated number of circulating times.

It is possible to simultaneously measure the intensity and the phase of the electric signal corresponding to the surface acoustic wave SAW at the predetermined designated number of circulating times as described above, and it is possible to measure one of them first and to measure the other second. Even when the intensity and the phase are measured with such a time difference, no practical problem occurs.

FIGS. 6A and 6B show results of experiments performed under the same conditions as those under which the experiments are performed and the results shown in FIGS. 4A and 4B are obtained by other yardsticks. From the experimental results, it is obvious that the phase of the electric signal corresponding to the surface acoustic wave does not react with the presence of hydrogen in the area having the hydrogen concentration which is equal to or less than 1.2%, and the hydrogen concentration cannot be measured from the phase. However, the intensity of the electric signal corresponding to the surface acoustic wave reacts with the presence of hydrogen even in the area having the hydrogen concentration which is equal to or less than 1.2%, and the hydrogen concentration which is equal to or less than 1.2% can be stably measured.

However, as obvious from the experimental result of FIG. 4B, it can be understood from the experimental result of FIG. 6B that the intensity of the electric signal corresponding to the surface acoustic wave does not react with the presence of hydrogen in the area having the hydrogen concentration which is equal to or more than 1.8%, and the concentration of hydrogen cannot be measured from the intensity.

Accordingly, if, in the low hydrogen concentration area where the hydrogen concentration is equal to or less than 1.2%, the hydrogen concentration is measured by using the intensity of the electric signal corresponding to the surface acoustic wave (change in an intensity of an electric signal corresponding to a surface acoustic wave, caused by a change in an attenuation amount of a circulating surface acoustic wave by a palladium (Pd) sensitive film), and in the high hydrogen concentration area where the hydrogen concentration is equal to or more than 1.8%, the hydrogen concentration is measured by using the change in the phase of the electric signal corresponding to the surface acoustic wave, the measurement for the hydrogen concentration can be performed more accurately and difficult to be affected by a deterioration of the reaction of the palladium (Pd) film to hydrogen.

In an area of the hydrogen concentration between 1.2% and 1.8%, the hydrogen concentration can be accurately measured and evaluated by using one or both of the phase and the intensity of the electric signal corresponding to the surface acoustic wave.

Further, in the hydrogen concentration area between 1.2% and 1.8%, more precise observation is performed as to how the phase and the intensity of the electric signal corresponding to the surface acoustic wave change when the hydrogen concentration changes. As schematically shown in FIG. 7A, when the hydrogen concentration increases, the phase quickly drops initially, its change rate becomes gradually small, and it takes long time until the phase completely saturates. On the other hand, as schematically shown in FIG. 7B, when the hydrogen concentration increases, the intensity drops very steeply to reach a saturated state. This can be interpreted that the phase and the intensity of the electric signal corresponding to the surface acoustic wave are different from each other in their reaction speeds to the hydrogen concentration because the phase and the intensity of the electric signal corresponding to the surface acoustic wave respond to the hydrogen concentration by different mechanisms.

On the other hand, in the dropping process of the hydrogen concentration, as the phase steeply drops to a level of 0%, and the intensity drops slowly at first and then steeply toward the concentration level of 0%, it takes a long time until an output value becomes stable.

From the above experimental results, it is obvious that, if a value of the hydrogen concentration evaluated from the phase value is selected in the rising process of the hydrogen concentration and a value of the hydrogen concentration evaluated from the intensity value is selected in the dropping process of the hydrogen concentration, the hydrogen concentration measurement can be performed more faster.

The value of the hydrogen concentration between 1.2% and 1.8%, at which response characteristics of the intensity and the phase of the electric signal corresponding to the surface acoustic wave change, is not always constant. In this case, however, the hydrogen concentration can be measured more accurately with high-performance by outputting measurement results of the phase and the intensity selectively or with changing weight thereof in accordance with an absolute concentration or its changing direction (concentration increasing direction or concentration decreasing direction) through a proper algorithm.

The hydrogen sensitive film of palladium (Pd) can be formed by using a material containing other substances such as nickel (Ni) in the palladium (Pd), and it is known that the material can make a speed of reaction to hydrogen being faster and can make a phase transition from an α phase to a β phase being difficult.

Figure 8:
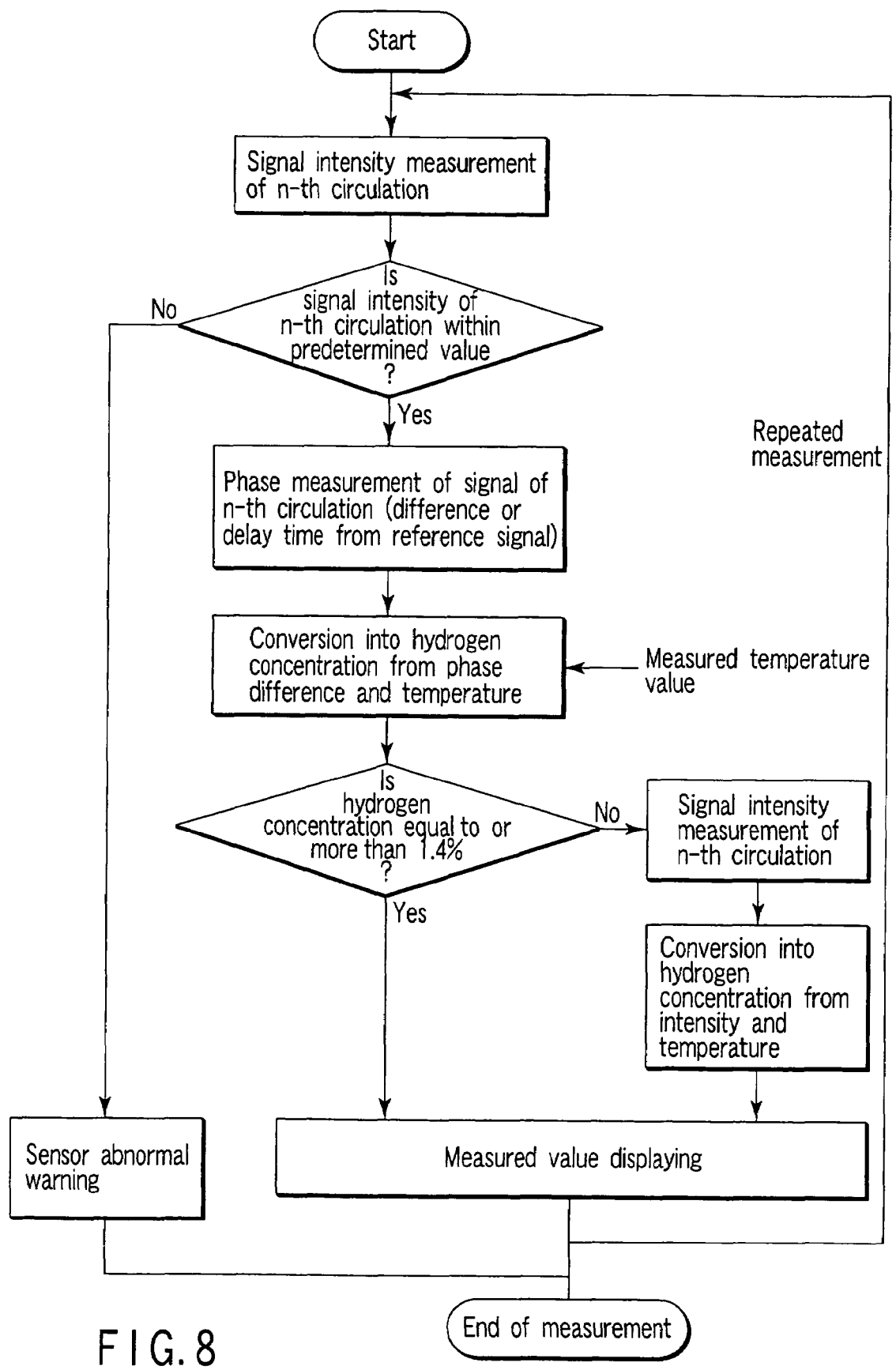
FIG. 8 shows an algorithm of a self-diagnosis and hydrogen concentration measurement in the environment difference detector according to the embodiment of the present invention.
Figure 9:
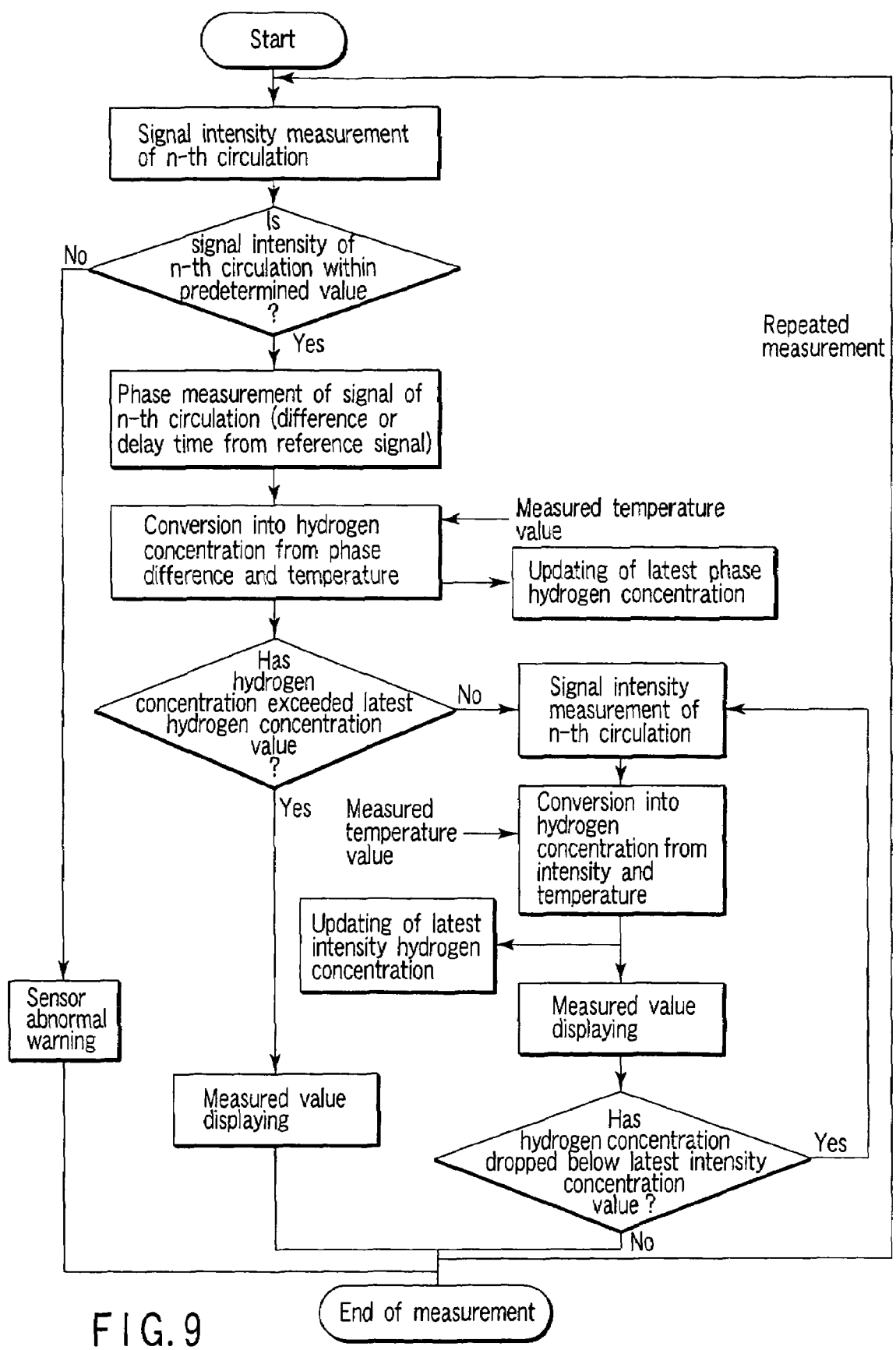
FIG. 9 shows an example of an algorithm which enables a highly accurate hydrogen concentration measurement by contriving a method of selecting one of hydrogen concentration values measured on a basis of the phase and the intensity of the surface acoustic wave when the hydrogen concentration increases and decreases in the environment difference detector according to the embodiment of the present invention.

FIG. 8 shows an algorithm of a series of self-diagnosis and hydrogen concentration measurement described above. And, FIG. 9 shows an example of an algorithm which can highly accurate measurement by contriving a method for selecting a hydrogen concentration value measured on a basis of the phase or the intensity when the hydrogen concentration increases or decreases.

EXAMPLE 1

(soundness of the environment difference detector is evaluated by using the intensity of the circulating signal):

The environment difference detector must be brought into contact with a surrounding environment but it may not be placed under an environment considered at a designing stage. For example, when a user places the detector under an environment where deterioration of the sensitive film and/or that of a wiring line is accelerated, by mistake, the sensitive film and/or the wiring line deteriorates. The deterioration of this kind generally causes an increase in resistance value. When such a change occurs, a changing ratio of the phase value is larger than that of the intensity value, and the deterioration of this kind reduces the intensity. Accordingly, when the intensity takes a value in a range which does not be taken in a sound state, an abnormality of the environment difference detector is determined and a warning is issued.

As another example, when a foreign object such as dust sticks on the sensitive film, energy of the surface acoustic wave is greatly lost. In this case, depending on a size of the foreign object, a large foreign object greatly changes the phase and the intensity of the surface acoustic wave. In this state, the environment difference detector cannot function as originally designed. Thus, an abnormality of the environment difference detector is determined and a warning is issued.

EXAMPLE 2

(depending on whether the hydrogen concentration is above or low 1.4%, selection is made as to which of the phase value and the intensity value of the electric signal corresponding to the surface acoustic wave is used to measure the hydrogen concentration):

In a case that the sensitive film is made of palladium, a change of the intensity disappears when the hydrogen concentration is above 1.4%. Thus, when the intensity reaches certain value or more, the hydrogen concentration is calculated by using the phase value of the electric signal corresponding to the surface acoustic wave. Conversely, when a change of the phase disappears and the phase change becomes a certain value or less, the hydrogen concentration is obtained on a basis of the intensity. As a result, the hydrogen concentration is measured more accurately.

In a case that the sensitive film is made of an alloy containing palladium, the hydrogen concentration which makes the intensity change disappears is different from 1.4%. However, the hydrogen concentration can be accurately obtained for the same method as described above.

EXAMPLE 3

(hydrogen concentration can be detected highly accurately by making proper selection as to which of the phase and the intensity of the electric signal corresponding to the surface acoustic wave is used to measure the hydrogen concentration when the hydrogen concentration rises or falls)

When the hydrogen concentration rises with time, following-ability of the intensity change to the change of the hydrogen concentration is better than that of the phase change in the electric signal corresponding to the surface acoustic wave. Accordingly, the hydrogen concentration is detected on a basis of a value of the intensity. Conversely, when the hydrogen concentration falls with time, following-ability of the phase change to the change of the hydrogen concentration is better than that of the intensity change in the electric signal corresponding to the surface acoustic wave. Accordingly, the hydrogen concentration is detected on a basis of a value of the phase. For detecting hydrogen leakage, since the hydrogen concentration rises, the concentration is calculated by using the value of the intensity. And, it is determined that whether the concentration exceeds a threshold. This achieves a fast and highly accurate leakage detection with making good use of characteristics of the environment difference detector.

For the response characteristic of the palladium sensitive film to hydrogen, it is expected that, when the palladium sensitive film is made of an alloy of palladium and nickel or the like, an influence of the response characteristic to the change of the intensity (attenuation rate) of the circulating surface acoustic wave which corresponds to the change of the environment is different from an influence of the response characteristic to the phase (circulating speed) of the circulating surface acoustic wave which corresponds to the change of the environment. For example, when the hydrogen concentration becomes high up to, e.g., several tens %, an influence of a change in such a high hydrogen concentration on the change of the phase (circulating speed) becomes small, but the influence on the change of the intensity (attenuation rate) becomes large. In this case, it is good to measure the change of the hydrogen concentration, i.e., the environmental change, by using the change of the intensity (attenuation rate) rather than the change of the phase (circulating speed). Accordingly, when the hydrogen concentration is measured, it is not always necessary to follow the aforementioned algorithm to use, i.e., select, the change of the intensity (attenuation rate) and the change of the phase (circulating speed) of the surface acoustic wave as a base for evaluating the environmental change.

Thus, in the present invention, by using one of the change of the intensity (attenuation rate) and the change of the phase (circulating speed) of the surface acoustic wave or both of them in accordance with characteristics of the sensitive film, it is possible to improve accuracy of the measurement of the environment to be measured (including adsorption and absorption of substances from the environment to be measured), to shorten measuring time, and to remove other factors causing measurement errors from the environment to be measured.

FIGS. 10A to 10D schematically show sectional views of first to fourth steps for manufacturing an elastic surface wave element unit in which two elastic surface wave elements 18 and 18' are incorporated for hydrogen measurement and for temperature calibration, the unit being used in a concrete example of the environment difference detector according to the embodiment of the present invention.

In these drawings, components similar to those of the spherical elastic surface wave element 18 shown in FIG. 1 are denoted by similar reference numerals, and detailed description thereof will be omitted.

FIG. 10A shows a state in which the elastic surface wave element 18 for the hydrogen concentration measurement and the elastic surface wave element 18' for the temperature calibration are fixed to predetermined positions on an inner surface of a protective container 26 by gold bumps. Each of the substrates 12 and 12' of each of these elastic surface wave elements 18 and 18' is made of rock crystal having a diameter of 1 mm. Each of the surface acoustic wave exciting/receiving units 14 and 14' of each of the two elastic surface wave elements 18 and 18' is connected to a predetermined wiring pattern prearranged in the protective container 26. An earth wire is omitted in the drawing. The protective container 26 uses a ceramic package for packaging a normal IC.

Next, as shown in FIG. 10B, an opening of the protective container 26 is covered with a sensor cover 50, and a predeposition unit which houses the two elastic surface wave elements 18 and 18' is configured. The sensor cover 50 is made of glass with a thickness of 0.1 mm, and has two holes each of which has a diameter of 0.3 mm. Each hole is used for exposing at least one part of each of the circular paths 12a and 12'a excluding the surface acoustic wave exciting/receiving units 14 and 14' on the two elastic surface wave elements 18 and 18' fixed at the predetermined positions on the inner surface of the protective container 26. When the opening of the protective container 26 is covered with the sensor cover 50, the surface acoustic wave exciting/receiving units 14 and 14' on the circular paths 12a and 12a' of the two elastic surface wave elements 18 and 18' must be positioned not to be seen through the corresponding holes. If the surface acoustic wave exciting/receiving units 14 and 14' on the circular paths 12a and 12a' of the elastic surface wave elements 18 and 18' are positioned to be seen through the holes, and the sensitive films 16 are formed as described below on parts of the circular paths 12a and 12a' of the elastic surface wave elements 18 and 18' corresponding to the holes, with using electrically conductive material, the conductive sensitive films 16 are electrically short-circuited with the surface acoustic wave exciting/receiving units 14 and 14' and make the surface acoustic wave exciting/receiving units 14 and 14' being disable to excite surface acoustic waves.

Next, in FIG. 10C, electric signals are actually supplied to the surface acoustic wave exciting/receiving units 14 and 14' on the circular paths 12a and 12a' of the two elastic surface wave elements 18 and 18' fixed at the predetermined positions on the inner surface of the protective container 26 and covered with the sensor cover 50, through the predetermined wiring pattern and the gold bumps prearranged in the protective container 26, to excite and circulate surface acoustic waves along the circular paths 12a and 12a', and outputs thereof are evaluated. At this time, if the outputs are not enough for desired values or the signal intensity decreases quickly with the circulation of the wave, it is determined that the surface acoustic wave exciting/receiving units 14 and 14' are not properly formed along crystal faces of rock crystals constituting the substrates 12 and 12' or foreign objects stick on the circular paths 12a and 12a' and obstruct the circulations of the surface acoustic waves, and further assembling steps will not be performed.

Figure 10D:
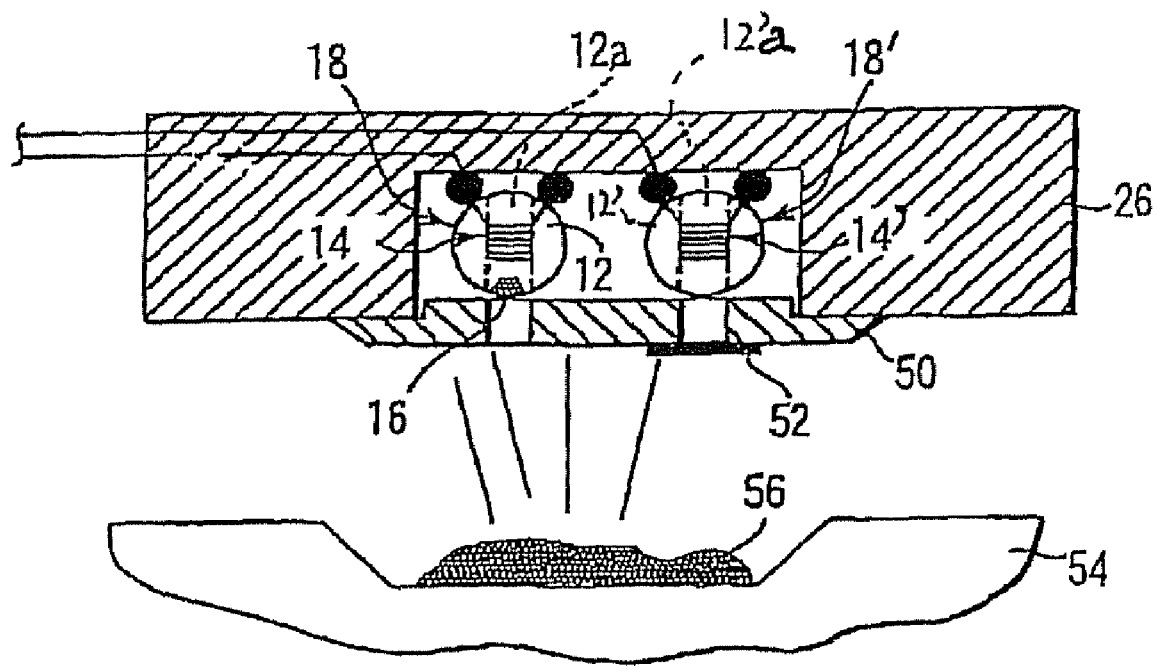
FIG. 10D is a figure showing a section of a fourth step of a manufacturing method for an elastic surface wave element unit used in a concrete example of the environment difference detector according to the embodiment of the present invention, the elastic surface wave element unit being incorporated with two elastic surface wave elements for hydrogen concentration measurement and for a temperature calibration.

Next, as shown in FIG. 10D, the predeposition unit configured by the protective container 26 in which the two elastic surface wave elements 18 and 18' are fixed at the predetermined positions on the inner surface and the opening is covered with the sensor cover 50, is set in an electric resistance heating vacuum deposition device. At this time, in the sensor cover 50, only the hole corresponding to the elastic surface wave element 18' for the temperature calibration is covered with a mask 52 while the hole corresponding to the elastic surface wave element 18 for the hydrogen concentration measurement is not covered with anything. Then, a heater 54 for an electric resistance heating deposition is heated in a vacuum environment to evaporate palladium 56, and palladium is deposited with a desired thickness (20 nm in this example) on a part of the circular path 12a of the substrate 12 of the elastic surface wave element 18 for the hydrogen concentration measurement, the part facing the hole, to form the sensitive film 16 with the desired thickness.

Next, a postdeposition unit configured by the protective container 26, in which the two elastic surface wave elements 18 and 18' are fixed at the predetermined positions on the inner surface and the opening of the container 26 is covered with the sensor cover 50, and further the palladium sensitive film 16 is formed on the part of the circular path 12a on the substrate 12 of the elastic surface wave element 18 for the hydrogen concentration measurement as described above, is taken out from the electric resistance heating vacuum deposition device, and then the mask 52 is removed.

Figure 11:
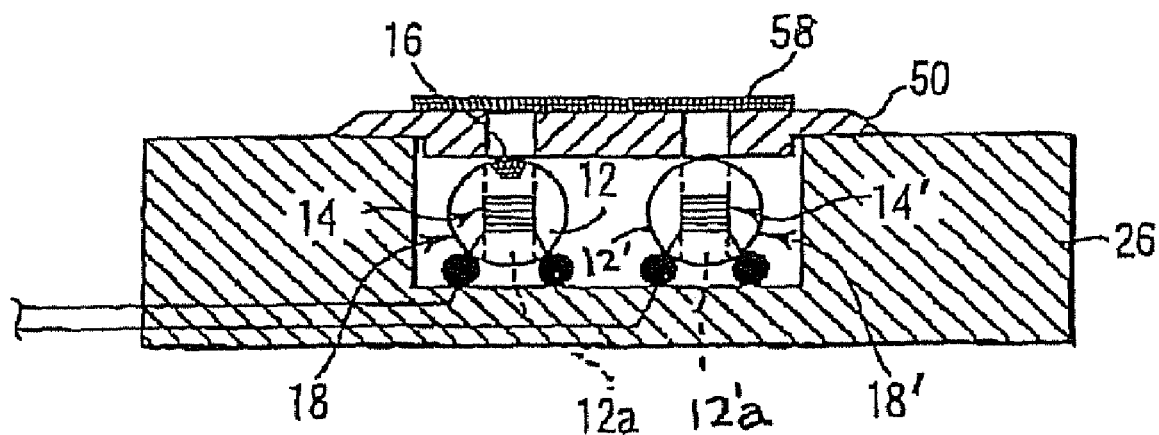
FIG. 11 is a schematic sectional view of the elastic surface wave element unit manufactured through the first to fourth steps shown in FIGS. 10A to 10D and used in a concrete example of the environment difference detector according to the embodiment of the present invention, the elastic surface wave element unit being incorporated with two elastic surface wave elements for hydrogen concentration measurement and for a temperature calibration.

Lastly, as shown in FIG. 11, the two holes of the sensor cover 50 are covered with a hydrogen transmissive film 58 such as a PET film having the thickness of 5-micron and being used for transmitting hydrogen only, whereby an elastic surface wave element unit, which is incorporated with the two elastic surface wave elements 18 and 18' for the hydrogen concentration measurement and for the temperature calibration and which is used in the environment difference detector according to the embodiment of the present invention, is completed.

By manufacturing the elastic surface wave element unit, which is incorporated with the two elastic surface wave elements 18 and 18' for the hydrogen concentration measurement and for the temperature calibration and which is used in the environment difference detector according to the embodiment of the present invention, in accordance with the steps described above with reference to FIGS. 10A to 10D and FIG. 11, a mask for depositing the sensitive film 16 is not necessary when the palladium sensitive film 16 is formed on a desired part of the circular path 12a of the substrate 12 of the elastic surface wave element 18 for the hydrogen concentration measurement by deposition, and, needless to say, a troublesome work for aligning the depositing mask with the part is not necessary. Besides, the sensor cover 50 can be used as a base to place the hydrogen transmissive film 58 for protecting the sensitive film 16 and the two elastic surface wave elements 18 and 18' for the hydrogen concentration measurement and for the temperature calibration. Moreover, in the deposition using expensive palladium, it is very useful for reducing not only material costs but also various heating and lighting costs which are necessary for deposition.

In the present invention, it is expressed that the circulating speed and the intensity are measured. This does not mean that it is necessary to simultaneously obtain numerical values of the both in one measurement, and it is not always necessary to measure and determine the both in one measurement. The detector may determine that one or both of the phase and the intensity are observed to make judgment, and analyze one numerical value alone as a result of the determination to output a measurement result.

In the present invention, the measurement of the circulating speed includes observation of only relative numerical values such as a difference obtained by comparison of circulating speeds among a plurality of elements or paths. It is because that an actually measured value can be measured on a basis of changing rates the circulating speed and the phase rather than absolute values thereof in many cases. Also, the measurement of the intensity may be a difference relative to a signal intensity of another reference element or that of another circulating path on the same element, and especially a ratio of weakening (attenuation ratio) of a signal as it circulates is important for evaluating an environment difference from a propagation state of an actual surface acoustic wave in most cases. Needless to say, when an exciting intensity is stable, measurement is possible by observing intensity at a specific circulating time, and even intensity measurement between two points can apparently be evaluated on a basis of intensity of the propagating state of the surface acoustic wave.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An environment difference detector, comprising:
an elastic surface wave element equipped with a substrate including a surface having at least one annular and circular path along which a surface acoustic wave circulates, a surface acoustic wave exciting/receiving unit exciting a surface acoustic wave along the circular path and receiving the surface acoustic wave excited and circulated along the circular path, and a sensitive film disposed on at least one part of the circular path to change an elastic nature in accordance with a predetermined change in an adjacent environment;
a speed/intensity measuring unit measuring a circulating speed and intensity of the surface acoustic wave from an electric signal generated by the surface acoustic wave exciting/receiving unit when the surface acoustic wave exciting/receiving unit receives the surface acoustic wave circulating along the circular path; and
an environment evaluation unit evaluating the predetermined change in the environment adjacent to the sensitive film from at least one of the circulating speed and the intensity measured by the speed/intensity measuring unit,
wherein the speed/intensity measuring unit measures the circulating speed from the electric signal by using at least one of circulating speed corresponding values selected from a group including a phase shift of the surface acoustic wave circulated along the circular path, a delay time of the circulated surface acoustic wave, and a resonance frequency of the circulated surface acoustic wave at which the vibration intensity of the circulated surface acoustic wave becomes maximum,
the predetermined change of the environment to be measured includes a plurality of ranges, and
the environment evaluation unit uses at least one of the circulating speed and the intensity, which is most suitable to evaluate the predetermined change in each of the ranges of the predetermined change of the environment to be measured.

2. The environment difference detector according to claim 1, wherein the surface of the substrate is a sphere.

3. The environment difference detector according to claim 1, wherein the speed/intensity measuring unit measures the intensity on a basis of an attenuation rate of the surface acoustic wave while the surface acoustic wave circulates.

4. The environment difference detector according to claim 1, wherein, the plurality of ranges includes at least one range in which the environment evaluation unit can evaluate the predetermined change most suitably by using both of the circulating speed and the intensity, and in the at least one range, the speed/intensity measuring unit measures one of the circulating speed and the intensity, and determines whether the other measuring result is correct.

5. The environment difference detector according to claim 1, wherein the sensitive film contains a material which is reactive to a gas, and reacts to the gas to change at least one of the circulating speed and the intensity of the surface acoustic wave circulating along the circular path, and the predetermined change of the environment adjacent to the sensitive film, evaluated from at least one of the circulating speed and the intensity measured by the speed/intensity measuring unit, is a gas concentration.

6. The environment difference detector according to claim 5, wherein the environment evaluation unit evaluates the gas concentration from at least one of the circulating speed and the intensity, which can evaluate the rising gas concentration most suitably while the gas concentration increases, and the environment evaluation unit evaluates the gas concentration from at least the other of the circulating speed and the intensity, which can evaluate the decreasing gas concentration most suitably while the gas concentration decreases.

7. The environment difference detector according to claim 5, wherein the sensitive film contains a material which is reactive to hydrogen, and the material which is contained in the sensitive film and which is reactive to hydrogen contains palladium, a hydrogen concentration is evaluated from the change of the intensity while the hydrogen concentration increases, and the hydrogen concentration is evaluated from the change of the phase corresponding to the circulating speed while the hydrogen concentration decreases.

8. The environment difference detector according to claim 5, wherein the material which is contained in the sensitive film and which is reactive to hydrogen contains palladium, the predetermined change of the environment is a change of the hydrogen concentration, the hydrogen concentration is evaluated from the intensity measured by the speed/intensity measuring unit in a range while the hydrogen concentration is equal to or less than a predetermined first concentration, the hydrogen concentration is evaluated from the circulating speed measured by the speed/intensity measuring unit in a range while the hydrogen concentration is equal to or higher than a predetermined second concentration which is higher than the first concentration, and the hydrogen concentration is evaluated from at least one of the circulating speed and the intensity, each measured by the speed/intensity measuring unit, in a range while the hydrogen concentration is between the first concentration and the second concentration.

9. The environment difference detector according to claim 8, wherein, in that the hydrogen concentration being equal to or less than the predetermined first concentration includes a hydrogen concentration of 1.0%, and the hydrogen concentration being equal to or more than the predetermined second concentration is a hydrogen concentration of 1.8% or more.

10. The environment difference detector according to claim 1, wherein the elastic surface wave element includes a plurality of circular paths, a plurality of surface acoustic wave exciting/receiving units corresponding to the plurality of circular paths, and a sensitive film disposed on at least one part of at least one of the plurality of circular paths.

11. The environment difference detector according to claim 1, wherein a plurality of elastic surface wave elements are used.

12. The environment difference detector according to claim 1, the detector further comprising a protective container which houses the elastic surface wave element while exposing the sensitive film, and wherein the elastic surface wave element equipped with the surface acoustic wave exciting/receiving unit is housed in the protective container before the sensitive film is disposed, and the sensitive film is disposed on at least one part of the circulating path of the substrate from the outside of the protective container after the substrate is housed in the protective container and it is checked that the surface acoustic wave exciting/receiving unit can excite and circulate a surface acoustic wave along the circular path.

13. The environment difference detector according to claim 12, wherein the protective container houses one elastic surface wave element without the sensitive film to expose at least one part of the circular path, the elastic surface wave element without the sensitive file, together with the elastic surface wave element to be disposed with the sensitive film, is housed in the protective container, and the elastic surface wave element without the sensitive film is not disposed with the sensitive film when the sensitive film is disposed on the elastic surface wave element to be disposed with the sensitive film.

* * * * *